United States Patent [19]

Katsumata et al.

[11] 4,456,563
[45] Jun. 26, 1984

[54] PROCESS FOR PRODUCING MALONONITRILE

[75] Inventors: Tsutomu Katsumata, Yokohama; Tetsuro Dozono, Yokosuka; Makoto Honda, Tokyo, all of Japan

[73] Assignee: Asahi Kasei Kogyo Kabushiki Kaisha, Osaka, Japan

[21] Appl. No.: 326,945

[22] Filed: Dec. 3, 1981

[30] Foreign Application Priority Data

Dec. 3, 1980 [JP] Japan .................................. 55-169481
Jan. 6, 1981 [JP] Japan ...................................... 56-82
Jan. 7, 1981 [JP] Japan .................................... 56-511
Sep. 8, 1981 [JP] Japan ................................. 56-68285

[51] Int. Cl.³ .................. C07C 120/00; C07C 121/22
[52] U.S. Cl. ............................................. 260/465.8 R
[58] Field of Search ................................. 260/465.8 R

[56] References Cited

U.S. PATENT DOCUMENTS

| | | | |
|---|---|---|---|
| 2,388,218 | 10/1945 | Olin | 260/465.1 |
| 2,849,478 | 8/1958 | Zubay et al. | 260/465.9 X |
| 3,225,080 | 12/1965 | Nakagawa et al. | 260/465.1 X |
| 3,396,190 | 8/1968 | McClain et al. | 260/465.1 |
| 3,468,945 | 9/1969 | Edwards et al. | 260/465. 1 X |
| 3,719,701 | 3/1973 | Bach | 260/465.9 |
| 3,983,161 | 9/1976 | McConaghy, Jr. | 260/464 X |

*Primary Examiner*—Joseph Paul Brust
*Attorney, Agent, or Firm*—Wyatt, Gerber, Shoup, Scobey & Badie

[57] ABSTRACT

Malononitrile is prepared in a high yield by catalytic oxidative dehydrogenation of β-aminopropionitrile in a gaseous phase with molecular oxygen in the presence of a catalyst, comprising a oxide composition of, preferably, Mo and at least one other catalytic element, more preferably, of the empirical formula (I):

$$Mo_{12}Bi_{0.1-24}A_aB_bC_cD_dO_x \qquad (I)$$

wherein A=Fe and/or Cr, B=Ni, Co, Mn and/or Mg, C=alkali metals, alkaline earth metals, rare earth metals, Te, Tl, W and/or Pb, a=0.1–24, b=0–24, c=0–2 and d=0–5.

5 Claims, 2 Drawing Figures

PROCESS FOR PRODUCING MALONONITRILE

FIELD OF THE INVENTION

The present invention relates to a process for producing malononitrile. More particularly, the present invention relates to a process for producing malononitrile from β-aminopropionitrile by means of a gaseous phase oxidative dehydrogenation.

Malononitrile is useful as a material for producing various medicines, including vitamin $B_1$.

BACKGROUND OF THE INVENTION

It is known from U.S. Pat. Nos. 2,459,128 and 2,389,217 that malononitrile is produced by preparing cyanoacetamide from monochloroacetic acid and sodium cyanide and, then, by converting cyanoacetamide to malononitrile by means of dehydration.

In this process, sodium cyanide, which is virulently poisonous and, therefore, should be extremely carefully handled, is used. Also, the process is composed of a plurality of steps. Furthermore, in the step of dehydrating cyanoacetamide, it is necessary to use an expensive additional material. Therefore, the above-mentioned process is unsatisfactory from the point of view of industrial utility.

Also, it is known from U.S. Pat. Nos. 2,553,406 and 2,606,917 and British Pat. No. 1,228,540 that malononitrile is prepared by reacting acetonitrile with cyanogen chloride at an elevated temperature of from 800° to 1000° C. This process is disadvantageous in the following ways. That is, since the reaction for producing malononitrile is carried out at a high temperature of from 800° to 1000° C., the reaction should be effected in a specific heat-resistant apparatus, which is expensive. Also, the high temperature reaction causes the reaction product to be contaminated with by-products, for example, carbon and polymers. Furthermore, the reaction product contains maleonitrile and fumaronitrile, which have boiling points close to that of malononitrile. Therefore, it is difficult to separate and purify malononitrile from maleonitrile and fumaronitrile by a usual separating and purifying method.

Furthermore, Japanese Patent Application Publication (Kokoku) No. 47-28968 (1972) discloses a process for producing malononitrile by the catalystic ammonoxidation of β-aminopropionitrile in the presense of ammonia and a catalyst. However, this process is disadvantageous in the following ways. That is, the yield of malononitrile is unsatisfactorily poor. The ammonoxidation reaction can be effected only in the presence of a large amount of ammonia. Accordingly, in the process, not only a large amount of ammonia is consumed, but also, a large amount of a neutralizing agent is used for neutralizing the reaction mixture. This feature makes it necessary to apply a complicated treatment to the waste water from the process and the cost of the process becomes undesirably high. Furthermore, when the resultant malononitrile is separated and recovered from the reaction mixture containing a large amount of ammonia, it is unavoidable that a portion of the resultant malononitrile becomes lost, because an alkaline substance added into an aqueous solution of malononitrile causes malononitrile to be remarkably chemically unstable and to be polymerized in the alkaline aqueous solution. Moreover, the large amount of ammonia in the reaction mixture causes the catalytic activity of the catalyst to decrease with the lapse of the reaction time.

SUMMARY OF THE INVENTION

An object of the present invention is to provide a method for catalytically producing malononitrile in a single step reaction without using poisonous substances.

Another object of the present invention is to provide a method for catalytically producing malononitrile at a relatively low temperature with a satisfactory yield thereof.

The above-mentioned objects can be attained by the method of the present invention which comprises subjecting β-aminopropionitrile to an oxidative dehydrogenation in a gaseous phase with molecular oxygen.

The resultant malononitrile can be collected from the reaction mixture by rapidly cooling the reaction mixture to a temperature of 80° C. or less to condense the malononitrile.

BRIEF DESCRIPTION OF THE INVENTION

DETAILED DESCRIPTION OF THE INVENTION

Figure 1:
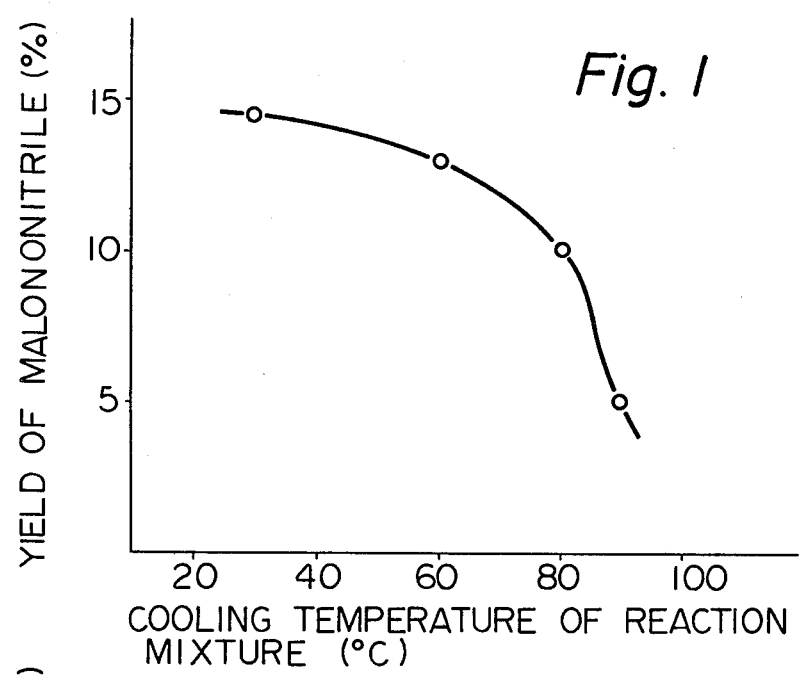
FIG. 1 is a graph showing a relationship between the cooling temperature applied to a reaction mixture and the yield of malononitrile.

In the method of the present invention, β-aminopropionitrile ($NH_2CH_2CH_2CN$) is oxidatively dehydrogenated in a gaseous phase with oxygen gas or an oxygen-containing gas. The oxidative dehydrogenation reaction can be promoted by using a catalyst comprising at least one oxide of at least one member selected from the group consisting of molybdenum (Mo), vanadium (V), tungsten (W), bismuth (Bi), iron (Fe), chromiun (Cr), nickel (Ni), cobalt (Co), manganese (Mn), tin (Sn), antimony (Sb), zinc (Zn), Copper (Cu), titanium (Ti) and other elements.

It is preferable that the oxidative dehydrogenation reaction be carried out in the presence of a catalyst comprising an oxide composition of molybdenum and at least one member selected from the group consisting of titanium, vanadium, chromiun, manganese, iron, cobalt, nickel, aluminium (Al), tin, antimony, tellurium (Te), bismuth, thallium (Tl), phosphorus (P), boron (B), alkali metals, alkaline earth metals and rare earth metals.

It is more preferable that the catalyst for the oxidative dehydrogenation consists essentially of an oxide composition of the empirical formula (I):

$$Mo_{12}Bi_{0.1-24}A_aB_bC_cD_dO_x \qquad (I)$$

wherein A represents at least one member selected from the group consisting of iron and chromium; B represents at least one member selected from the group consisting of nickel, cobalt, manganese and magnesium; C represents at least one member selected from the group consisting of alkali metals, alkaline earth metals, rare earth metals, tellurium, thallium, tungsten and lead; D represents at least one member selected from the group consisting of phosphorus, arsenic and boron; a represents the number 0.1 to 24; b represents the number 0 to 24; c represents the number 0 to 2; d represents the number 0 to 5, and; x represents the number of oxygen atoms which satisfies the valency of the catalytic elements in the oxide composition.

The catalyst for the present invention can be used in the form of the catalyst alone or in the form of a composite in which the catalyst is carried on a carrier consisting of silica, alumina, diatomaceous earth and/or pumice.

In the method of the present invention, it is preferable that a feed containing β-aminopropionitrile and oxygen gas or an oxygen-containing gas, for example, air, be brought into contact with the catalyst. The feed may contain steam and/or an inert gas in addition to β-aminopropionitrile and a molecular oxygen gas or a molecular oxygen-containing gas. The contact of the feed with the catalyst can be carried out in a fixed bed or a fluidized bed.

The oxidative dehydrogenation reaction in the method of the present invention is preferably carried out at a temperature of 350° C. or more, more preferably, from 350° to 550° C., and still, more preferably, from 380° to 500° C. When the oxidative dehydrogenation reaction is carried out by using the catalyst, it is preferable that the contact time of the feed with the catalyst be in the range of from 0.01 to 20 seconds, more preferably, from 0.05 to 5 seconds.

In the method of the present invention, it is preferable that the molar ratio of β-aminopropionitrile to molecular oxygen be in a range of from 1:0.5 to 1:10, more preferably, from 1:1 to 1:5.

The oxidative dehydrogenation reaction in the method of the present invention may be carried out under any pressure. However, it is preferable that the reaction be carried out under a pressure of 1 to several atmospheres.

As stated above, malononitrile is chemically unstable. Therefore, it is important to collect the resultant malononitrile from the resultant reaction mixture without allowing malononitrile to be lost. For this purpose, it is preferable to rapidly cool the reaction mixture containing the resultant malononitrile to a temperature of 80° C. or less, more preferably, 60° C. or less, so as to allow the resultant malononitrile to condense.

If the resultant malononitrile is collected from the reaction mixture at a temperature exceeding 80° C., the yield of malononitrile is significantly decreased. This feature is illustrated in FIG. 1.

Usually, the condensate of the resultant malononitrile is contaminated with unreacted β-aminopropionitrile. Therefore, the contaminated condensate exhibits an alkaline pH.

Under the alkaline condition, even if the temperature of the condensate is lower than 80° C., it is unavoidable that a portion of the malononitrile is polymerized and lost. Accordingly, in order to avoid the polymerization of malononitrile, it is desirable to adjust the pH of the condensate to a value of 7.0 or less, more preferably, 6.0 or less, still more preferably, 1.0 to 6.0, by adding an acid or acid substance to the reaction mixture or the condensation. If the resultant malononitrile is collected from the reaction mixture at a pH exceeding 7.0, the yield of malononitrile is very poor. This feature is clearly illustrated in FIG. 2. The acid may consist of at least one selected organic acid, for example, acetic acid or inorganic acid, for example, sulfuric acid.

The cooling procedure for the reaction mixture may be carried out by using a coolant which does not contaminate the resultant malononitrile and which is capable of being easily separated from the resultant malononitrile. For example, it is preferable that the coolant consists of water or a condensate from the reaction mixture.

In the cooling procedure, it is important that the reaction mixture be cooled as rapidly as possible to a temperature of 80° C. or less, preferably, 60° C. or less, at a cooling rate of 20° C./sec or more. The reaction mixture may be directly cooled by the coolant by injecting the coolant into the reaction mixture or by injecting the reaction mixture into the coolant. In the direct cooling procedure, it is preferable that the acid or acid substance be preliminarily added to the coolant, so that when the malononitrile is condensed, the pH of the condensation can be immediately adjusted to a desired value of 7.0 or less.

When the reaction mixture is indirectly cooled by the coolant, it is done by bringing the coolant into contact with a container into which the reaction mixture is supplied. In this case, it is preferable that the acid or acid substance be supplied in the form of a gas or spray into the container. Also, a portion of the coolant may be blown into the container to promote the rapid cooling of the reaction mixture.

Alternatively, the reaction mixture may be blown into a cooled neutral or acid solvent selectively to extract malononitrile from the reaction mixture.

In the cooling procedure, in order to prevent the acid corrosion of the reaction apparatus and/or the cooling apparatus, it is preferable that the acid or acid substance be used in an amount which does not cause the apparatus to become corroded. That is, it is preferable that the pH of the condensate containing the acid or acid substance is 7.0 or less, but not below 1.0.

When the method of the present invention is applied to β-aminopropionitrile, the resultant reaction mixture contains, in addition to malononitrile, the non-reacted β-aminopropionitrile, $CO_2$, CO and small amounts of acrylonitrile, acetonitrile and substances having a high boiling point. However, the reaction mixture contains no maleonitrile and fumaronitrile which are difficult to separate from malononitrile.

SPECIFIC EXAMPLES OF THE INVENTION

The specific examples set forth below will serve more fully to explain the practice of the process of the present invention. However, it should be understood that the examples are only illustrative and should in no way limit the scope of the present invention.

In the examples, the percent of conversion of β-aminopropionitrile and the percent of selectivity to malononitrile were calculated in accordance with the following equations.

Conversion of β-aminopropionitrile (%) =

$$\frac{\text{Molar amount of } \beta\text{-aminopropionitrile reacted}}{\text{Molar amount of } \beta\text{-aminopropionitrile supplied}} \times 100$$

Selectivity to malononitrile (%) =

$$\frac{\text{Molar amount of malononitrile produced}}{\text{Molar amount of } \beta\text{-aminopropionitrile reacted}} \times 100$$

EXAMPLES 1 THROUGH 4

In Example 1, a catalyst consisting essentially of molybdenum oxides was prepared in such a manner that one part by weight of ammonium heptamolybdate [$(NH_4)_6Mo_7O_{24} \cdot 4H_2O$] was dissolved in 2 parts by weight of water, the resultant solution was evaporated to dryness at a temperature of 130° C. and the resultant solid material was calcined at a temperature of 600° C. for 2 hours.

A glass reaction tube having an inside diameter of 8 mm was charged with 0.5 g of the above-mentioned catalyst.

A feed gas containing β-aminopropionitrile, molecular oxygen, nitrogen and steam in the molar ratio of 1:1.2:10:1, was flowed through the reaction tube, so as to bring the feed gas into contact with the catalyst for 0.15 seconds at a temperature of 440° C. under atmospheric pressure.

A portion of the resultant reaction gas mixture was subjected to a gas chromatographic analysis to determine the amounts of non-reacted β-aminopropionitrile and malononitrile.

In the results of the analysis, it was found that the conversion of β-aminopropionitrile was 98% and the selectivity to malononitrile was 15.5%. No maleonitrile and no fumaronitrile were detected in the resultant reaction mixture.

The same analysis as that mentioned above was applied to a portion of the reaction mixture obtained 10 hours after the start of the above-mentioned reaction procedure. The results of the analysis were the same as those mentioned above.

In each of the Examples 2, 3 and 4, the same procedures as those described in Example 1 were carried out, except that the reaction was carried out at temperatures indicated in Table 1. The results of the analysis are indicated in Table 1.

TABLE 1

| Example No. | Reaction temperature (°C.) | Conversion of β-aminopropionitrile (%) | Selectivity to malononitrile (%) |
|---|---|---|---|
| 2 | 420 | 85 | 7.5 |
| 3 | 460 | 100 | 15.8 |
| 4 | 480 | 100 | 6.1 |

COMPARATIVE EXAMPLE 1

The same procedures as those described in Example 1 were carried out, except that the feed gas contained β-aminopropionitrile, ammonia, molecular oxygen, nitrogen and steam in a molar ratio of 1:5:1.2:10:1.

The conversion of β-aminopropionitrile was 90% and the selectivity to malononitrile was 10.5%. That is, the addition of ammonia caused both the conversion of β-aminopropionitrile and the selectivity to malononitrile to decrease.

After the above-mentioned reaction procedure was continued for 10 hours, it was found that the conversion of β-aminopropionitrile decreased to 85% and the selectivity to malononitrile decreased to 7.5%. That is, it is evident that the addition of ammonia caused the catalytic activity of the catalyst used to decrease.

EXAMPLE 5

The same procedures as those described in Example 1 were carried out, except that the catalyst consisted of vanadium (V) oxide prepared by calcining ammonium metavanadate ($NH_4VO_3$) at a temperature of 550° C. for 4 hours and the reaction temperature was 400° C.

It was found that the conversion of β-aminopropionitrile was 100% and the selectivity to malononitrile was 1.5%.

EXAMPLE 6

The same procedures as those described in Example 1 were carried out with the following exception.

The catalyst used was prepared in such a manner that one part by weight of ammonium paratungstate $[5(NH_4)_2O.12WO_3.5H_2O]$ was dissolved in 30 parts by weight of a hot aqueous solution containing 10% by weight of oxalic acid; 2.9 parts by weight of a silica sol containing 30% by weight of $SiO_2$ were added to the above-mentioned aqueous solution; the mixture was evaporated to dryness at a temperature of 130° C.; and, then, the resultant dry solid material was calcined at a temperature of 600° C. for 2 hours. A catalyst, consisting essentially of tungsten oxides carried on a silica carrier, was obtained. The reaction temperature was 450° C.

As results of the reaction, the conversion of β-aminopropionitrile was 95% and the selectivity to malononitrile was 1.8%.

EXAMPLE 7

The same procedures as those described in Example 1 were carried out with the following exception.

The catalyst used was prepared in such a manner that one part by weight of a tin powder was dissolved in 20 parts by weight of an aqueous solution containing 20% by weight of nitric acid at a temperature of 100° C., and separately, 4.1 parts by weight of an antimony powder were dissolved in 6 parts by weight of an aqueous solution containing 60% by weight of nitric acid at a temperature of 100° C.; the tin solution was mixed with the antimony solution; the mixture was evaporated to dryness; and, then, the resultant dry solid material was calcined at a temperature of 700° C. for 16 hours. The resultant catalyst consisted essentially of an oxide composition in which the molar ratio of tin to antimony was 2:1.

The reaction temperature was 380° C.

It was found that the conversion of β-aminopropionitrile was 90% and the selectivity to malononitrile was 0.8%.

EXAMPLE 8

The same procedures as those described in Example 1 were carried out, except that the catalyst used was prepared by mixing a solution of one part by weight of nickel nitrate $[Ni(NO_3)_2.2H_2O]$ in 2 parts by weight of hot water with a solution of 1.4 parts by weight of chromiun nitrate $[Cr(NO_3)_2.9H_2O]$ in 3 parts by weight of hot water, by evaporating the mixture to dryness and by calcining the resultant dry solid material at a temperature of 500° C. for 2 hours, and the reaction was carried out at a temperature of 400° C.

It was calculated from the results of the analysis that the conversion of β-aminopropionitrile was 97% and the selectivity to malononitrile was 2.6%.

EXAMPLE 9

The same procedures as those described in Example 1 were carried out, except that the catalyst used was prepared by mixing a solution of one part by weight of ferric nitrate $[Fe(NO_3).9H_2O]$ in 1 part by weights of hot water with another solution of 1.5 parts by weight of an antimony powder in 9 parts by weight of an aqueous solution of 60% by weight of nitric acid having a temperature of 100° C.; by evaporating the mixture to dryness; and by calcining the resultant dry solid material at a temperature of 700° C. for 8 hours, with the reaction temperature being 380° C.

The conversion of β-aminopropionitrile was 91% and the selectivity to malononitrile was 2.4%.

EXAMPLE 10

Procedures identical to those described in Example 1 were carried out, except that the catalyst used was prepared in such a manner that one part by weight of ammonium metavanadate ($NH_4VO_3$) was dissolved in a hot aqueous solution of 10% by weight of oxalic acid; 18 parts by weight of an α-alumina powder were dispersed in the oxalic acid solution; the dispersion was evaporated to dryness; and, then, the resultant dry solid material was calcined at a temperature of 600° C. for 2 hours to obtain a vanadium oxide catalyst supported on alumina, with the reaction temperature being 490° C.

As results of the analysis, the conversion of β-aminopropionitrile was 98% and the selectivity to malononitrile was 5.5%.

EXAMPLE 11

The same procedures as those described in Example 1 were carried out, except that the catalyst was prepared in such a manner that one part by weight of nickel nitrate was dissolved in one part by weight of hot water; the solution was mixed with 4.8 parts by weight of an α-alumina powder; the mixture was evaporated to dryness; and, then, the dry solid material was calcined at a temperature of 600° C. for 2 hours, with the reaction temperature being 430° C.

The conversion of β-aminopropionitrile was 30% and the selectivity to malononitrile was 0.2%.

EXAMPLE 12

The same procedures as those described in Example 1 were carried out, except that one part by weight of manganese nitrate [$Mn(NO_3)_2.6H_2O$] was dissolved in one part by weight of hot water; the solution was mixed with 4.6 parts by weight of an α-alumina powder; the mixture was evaporated to dryness; and, finally, the dry solid material was calcined at a temperature of 600° C. for 2 hours, with the reaction temperature being 450° C.

The conversion of β-aminopropionitrile was 86% and the selectivity to malononitrile was 0.7%.

EXAMPLE 13

The same procedures as those described in Example 1 were carried out, except that the reaction temperature was 500° C. and the catalyst used was prepared by dissolving one part by weight of magnesium nitrate [$Mg(NO_3)_2.6H_2O$] in 2.5 parts by weight of hot water; by mixing the solution with 3 parts by weight of an α-alumina powder; by evaporating the mixture to dryness; and finally, by calcining the dry solid material at a temperature of 600° C. for 2 hours, to provide a magnesium oxide catalyst carried on α-alumina.

The conversion of β-aminopropionitrile was 100%, and the selectivity to malononitrile was 0.1%.

EXAMPLE 14

The same procedures as those described in Example 1 were carried out, except that the reaction temperature was 460° C. and the catalyst was prepared by dissolving one part by weight of a tin powder in 20 parts by weight of an aqueous solution containing 20% by weight of nitric acid; by mixing the resultant solution with 24 parts by weight of an α-alumina powder; by evaporating the mixture to dryness; and, finally by calcining the dry solid material at a temperature of 600° C. for 2 hours to provide a tin oxide catalyst carried on α-alumina.

The conversion of β-aminopropionitrile was 60% and the selectivity to malononitrile was 0.2%.

EXAMPLE 15

The same procedures as those described in Example 1 were carried out, except that the reaction temperature was 400° C. and the catalyst was prepared in such a manner that one part by weight of ferric nitrate was dissolved in 2 parts by weight of hot water; the solution was mixed with 3.7 parts by weight of an α-alumina powder; the mixture was evaporated to dryness; and, then, the resultant dry solid material was calcined at a temperature of 600° C. for 2 hours to provide an iron oxide catalyst carried on α-alumina.

The conversion of β-aminopropionitrile was 36% and the selectivity to malononitrile was 0.35%.

EXAMPLE 16

The same procedures as those described in Example 1 were carried out, except that the reaction temperature was changed to 490° C. and the catalyst was prepared by such a method that one part by weight of bismuth nitrate [$Bi(NO_3)_3.5H_2O$] was dissolved in one part by weight of an aqueous solution containing 20% by weight of nitric acid; the resultant solution was mixed with 6.4 parts by weight of an α-alumina powder; the mixture was evaporated to dryness; and, finally, the resultant dry solid material was calcined at a temperature of 600° C. for 2 hours to provide a bismuth oxide catalyst carried on α-alumina.

The conversion of β-aminopropionitrile was 75% and the selectivity to malononitrile was 0.1%.

EXAMPLES 17 THROUGH 40

In each of the Examples 17 through 40, a catalyst was prepared in a method as described hereinafter. A glass reaction tube having an inside diameter of 8 mm was filled with 0.5 g of the catalyst. A feed gas containing α-aminopropionitrile, molecular oxygen, nitrogen and steam in a molar ratio of 1:1.2:10:1, was flowed through the reaction tube at a temperature as indicated in Table 2, so as to allow the feed gas to contact the catalyst for 0.15 seconds.

A portion of the resultant reaction mixture was subjected to a gas chromatographic analysis. The results of the analysis are indicated in Table 2.

CATALYST USED IN EXAMPLE 17

The catalyst was prepared by calcining phosphorus molybdate at a temperature of 400° C. for 2 hours to provide an oxide composition of the empirical formula $Mo_{12}P_1O_x$.

CATALYST USED IN EXAMPLE 18

The catalyst was prepared by the following method. A solution A was prepared by dissolving one part by weight of ammonium heptamolybdate in 2 parts by weight of hot water at a temperature of 70° C. Separately, a solution B was prepared in such a manner that 0.146 parts by weight of ammonium metavanadate were gradually mixed into 1.46 parts by weight of an aqueous solution containing 20% by weight of oxalic acid at a temperature of 80° C. while the mixture was vigorously stirred, and, after the two items were thoroughly mixed, the stirring operation of the mixture was continued for about 20 minutes, until the resultant solution exhibited a dark navy blue color. Then, the solution A was mixed with the solution B. The mixed solution was further mixed with 3.45 parts by weight of an α-alumina powder. The mixture was evaporated to dryness. The resultant dry solid material was calcined at a temperature of 400° C. for 2 hours, to provide a catalyst of the empirical formula $Mo_{12}V_{1.33}O_x$, carried on α-alumina.

CATALYST USED IN EXAMPLE 19

The catalyst was prepared by dissolving one part by weight of ammonium heptamolybdate in 2 parts by weight of water at a temperature of 70° C.; by mixing the resultant solution with 3.96 parts by weight of a silica sol containing 30% by weight of silica; by additionally mixing the mixture with 0.373 parts by weight of a titanium dioxide powder; by evaporating the resultant mixture to dryness; and by calcining the resultant dry solid material at a temperature of 600° C. for 2 hours, to provide a catalyst of the empirical formula $Mo_{12}Ti_{10}O_x$, carried on silica.

CATALYST USED IN EXAMPLE 20

The catalyst was prepared in such a manner that one part by weight of ammonium heptamolybdate was dissolved in 2 parts by weight of water at a temperature of 70° C.; the resultant solution was mixed with 3.54 parts by weight of a 30 weight % silica sol; the mixture was further mixed with an aqueous solution of 1.31 parts by weight of chromium nitrate $[Cr(NO_3)_3 \cdot 9H_2O]$ in 2.5 parts by weight of water; the resultant mixture was evaporated to dryness; and, finally, the resultant dry solid was calcined at a temperature of 600° C. for 2 hours to provide a catalyst of the empirical formula $Mo_{12}Cr_{10}O_x$.

CATALYSTS USED IN EXAMPLES 21 THROUGH 40

Each of the catalysts used in Examples 21 through 40 was of the emprical formula as indicated in Table 2. The catalysts were prepared in the similar manner to that described in Example 19, by using boric acid, stannic oxide, diantimony trioxide, telluric acid, and/or nitrates of Mh, Mg, Cu, Bi, Co, Ni, Fe, Na, K, Al, Ce and/or Tl.

The calcining temperature of each catalyst is indicated in Table 2. The calcining time applied to each catalyst was 2 hours.

TABLE 2

| Example No. | Type of catalyst | Carrier | Calcining temperature (°C.) | Reaction temperature (°C.) | Conversion of β-aminopropionitrile (%) | Selectivity to malononitrile (%) |
|---|---|---|---|---|---|---|
| 17 | $Mo_{12}P_1$ | — | 400 | 400 | 100 | 24 |
| 18 | $Mo_{12}V_{1.33}$ | 80 wt % α-$Al_2O_3$ | 400 | 480 | 100 | 26 |
| 19 | $Mo_{12}Ti_{10}$ | 50 wt % $SiO_2$ | 600 | 400 | 100 | 22 |
| 20 | $Mo_{12}Cr_{10}$ | 50 wt % $SiO_2$ | 600 | 460 | 100 | 19 |
| 21 | $Mo_{12}Mn_{10}$ | 50 wt % $SiO_2$ | 600 | 460 | 100 | 13 |
| 22 | $Mo_{12}Mg_{10}$ | 50 wt % $SiO_2$ | 600 | 480 | 99 | 16 |
| 23 | $Mo_{12}Ca_{10}$ | 50 wt % $SiO_2$ | 600 | 455 | 100 | 10.5 |
| 24 | $Mo_{12}Bi_{12}$ | 50 wt % $SiO_2$ | 600 | 445 | 100 | 13 |
| 25 | $Mo_{12}Bi_9P_1$ | 50 wt % $SiO_2$ | 550 | 440 | 100 | 20 |
| 26 | $Mo_{12}Bi_9B_2$ | 50 wt % $SiO_2$ | 540 | 440 | 83 | 26 |
| 27 | $Mo_{12}Co_6$ | — | 600 | 475 | 100 | 15 |
| 28 | $Mo_{12}Ni_6$ | — | 600 | 460 | 99 | 12 |
| 29 | $Mo_{12}Fe_8$ | — | 600 | 435 | 100 | 13 |
| 30 | $Mo_{12}Sn_{28}$ | — | 500 | 430 | 90 | 23 |
| 31 | $Mo_{12}Sb_1$ | 50 wt % $SiO_2$ | 600 | 450 | 100 | 11 |
| 32 | $Mo_{12}Sb_{12}$ | 50 wt % $SiO_2$ | 600 | 475 | 99 | 9 |
| 33 | $Mo_{12}Te_6P_1$ | 50 wt % $SiO_2$ | 400 | 460 | 100 | 13 |
| 34 | $Mo_{12}Te_4Ce_3$ | 50 wt % $SiO_2$ | 440 | 400 | 100 | 12.5 |
| 35 | $Mo_{12}Te_{1.3}Fe_8$ | 50 wt % $SiO_2$ | 450 | 430 | 98 | 15 |
| 36 | $Mo_{12}Na_{0.5}$ | 50 wt % $SiO_2$ | 550 | 450 | 98 | 12 |
| 37 | $Mo_{12}K_{0.1}$ | 50 wt % $SiO_2$ | 550 | 450 | 100 | 14 |
| 38 | $Mo_{12}Al_6$ | 50 wt % $SiO_2$ | 600 | 450 | 100 | 17 |
| 39 | $Mo_{12}Bi_2Ce_4$ | — | 600 | 485 | 85 | 14 |
| 40 | $Mo_{12}Bi_9Tl_1$ | — | 600 | 470 | 98 | 16 |

EXAMPLES 41 THROUGH 54

In each of the Examples 41 through 54, the same procedures as those described in Example 17 were carried out, except that the catalyst was prepared in the method as described hereinafter, and the reaction was carried out at a temperature as indicated in Table 3. The results are indicated in Table 3.

CATALYST USED IN EXAMPLE 41

This catalyst was prepared in such a manner that 167 g of a silica sol containing 30% by weight of silica ($SiO_2$) was mixed with 1.7 g of an aqueous solution containing 85% by weight of phosphoric acid; the mixture was mixed with an aqueous solution which was prepared by dissolving 33 g of ammonium heptamolybdate in 65 g of water at a temperature of 60° C.; the resultant mixture was further mixed with a solution prepared by dissolving 30 g of bismuth nitrate, 44 g of ferric nitrate and 0.12 g of potassium nitrate in 30 g of an aqueous solution containing 13% by weight of nitric acid at a temperature of 50° C., while stirring the mixture; the resultant slurry was evaporated to dryness; and, finally, the resultant dry solid was calcined at a temperature of 690° C. for 2 hours. The resultant catalyst is of the empirical formula $Mo_{12}Bi_{4.3}Fe_{7.2}K_{0.075}P_1O_x$ and carried in an amount of 50% by weight on a silica carrier.

CATALYST USED IN EXAMPLE 42

This catalyst was prepared in the following manner. 167 g of a silica sol containing 30% by weight of silica were mixed with 1.5 g of an aqueous solution containing 85% by weight of phosphoric acid; this mixture was mixed with an aqueous solution prepared by dissolving 27.0 g of ammonium heptamolybdate in 54 g of water at a temperature of 60° C.; and, then, this was mixed with a solution prepared by dissolving 43.0 g of bismuth nitrate, 23.2 g of ferric nitrate, 7.5 g of cobalt nitrate and 1.1 g of sodium nitrate in 50 g of an aqueous solution containing 13% by weight of nitric acid at a temperature of 50° C., while stirring the mixture. The resultant slurry was evaporated to dryness and the resultant dry solid was calcined at a temperature of 690° C. for 2 hours. The resultant catalyst was of the empirical formula $Mo_{12}Bi_7Fe_{4.5}Co_2Na_1P_1O_x$, and carried in an amount of 50% on the silica carrier.

CATALYSTS USED IN EXAMPLES 43 THROUGH 54

The catalysts used in the Examples 43 through 54 were of the empirical formula as indicated in Table 3 and were prepared in the similar manner to that described in Examples 41 and 42, except that the calcining procedure was carried out at temperatures as indicated in Table 3 for 2 hours.

In the preparation of the catalysts, the source of Boron was boric acid; the source of tellurium was telluric acid; the source of tungsten was ammonium paratangstate; and the sources of the other elements were nitrates of those elements.

TABLE 3

| Example No. | Type of catalyst | Carrier | Calcining temperature (°C.) | Reaction temperature (°C.) | Conversion of β-amino-propionitrile (%) | Selectivity of malono-nitrile (%) |
|---|---|---|---|---|---|---|
| 41 | $Mo_{12}Bi_{4.3}Fe_{7.2}K_{0.075}P_1$ | 50 wt % $SiO_2$ | 690 | 450 | 99 | 42 |
| 42 | $Mo_{12}Bi_7Fe_{4.5}CO_2Na_1P_1$ | 50 wt % $SiO_2$ | " | 460 | 100 | 29 |
| 43 | $Mo_{12}Bi_1Fe_1Ni_1Rb_{0.1}$ | 50 wt % $SiO_2$ | 650 | 420 | 99 | 27 |
| 44 | $Mo_{12}Bi_1Fe_1Cr_1$ | 50 wt % $SiO_2$ | " | ' | 100 | 8 |
| 45 | $Mo_{12}Bi_2Fe_1Ce_1K_{0.1}$ | 50 wt % $SiO_2$ | " | ' | 100 | 25 |
| 46 | $Mo_{12}Bi_1Fe_1B$ | 50 wt % $SiO_2$ | ' | " | 100 | 20 |
| 47 | $Mo_{12}Bi_1Fe_1Ni_1Mg_1K_{0.1}$ | 50 wt % $SiO_2$ | 530 | 430 | 100 | 23 |
| 48 | $Mo_{12}Bi_1Fe_1Ni_1Mn_1Co_1K_{0.1}$ | 50 wt % $SiO_2$ | ' | " | 100 | 9 |
| 49 | $Mo_{12}Bi_1Fe_1Ni_1Pb_1$ | 50 wt % $SiO_2$ | " | " | 99 | 28 |
| 50 | $Mo_{12}Bi_1Fe_1Ni_7Te_{0.2}$ | 50 wt % $SiO_2$ | " | 450 | 100 | 20 |
| 51 | $Mo_{12}Bi_1Fe_{1.5}Cr_1Ni_7K_{0.3}$ | 50 wt % $SiO_2$ | 600 | ' | 99 | 25 |
| 52 | $Mo_{12}Bi_1Fe_1Ni_7Ba_1P_{0.3}$ | 50 wt % $SiO_2$ | " | ' | 100 | 25 |
| 53 | $Mo_{12}Bi_1Fe_1Ni_7W_1P_{0.3}$ | 50 wt % $SiO_2$ | ' | " | 100 | 26 |
| 54 | $Mo_{12}Bi_1Fe_1Ni_7Tl_{0.3}P_{0.3}$ | 50 wt % $SiO_2$ | ' | " | 100 | 29 |

EXAMPLE 55

A reaction tube having an inside diameter of 19 mm and a length of 50 cm was filled with 25 g of the same catalyst as that described in Example 1. A feed gas containing β-aminopropionitrile, molecular oxygen, nitrogen and steam in the molar ratio of 1:1.2:10:5, was flowed through the reaction tube at a temperature of 440° C. under atmospheric pressure, so as to allow the feed gas to contact the catalyst for 0.2 seconds. The entire amount of the resultant reaction mixture discharged from the reaction tube was introduced into a rapid cooling vessel having a capacity of two liters and containing one liter of water, so that the resultant malononitrile was absorbed by the water. The temperature of the water in the vessel was maintained at 30° C. Also, the pH of the water was maintained at a value of 5.0 by adding an aqueous sulfuric acid solution.

After the absorbing operation was continued for one hour, the absorbing liquid was subjected to a gas chromatographic analysis to determine the amount of malononitrile produced. As a result of the analysis, the yield of malononitrile was 14.5%.

This value of the yield of 14.5% was the same as that determined by using a portion of the resultant reaction mixture collected at the outlet of the reaction tube. That is, no loss of the resultant malononitrile occurred in the water-absorbing procedure.

The same procedures as those described above were repeated, except that the pH of water in the vessel was not controlled by adding sulfuric acid. After the absorbing operation was continued for one hour, the pH of the water was 9.8 and the yield of malononitrile was 3.0%. Also, it was found that a solid material, which appeared to be an undesirable polymerization product of malononitrile, was deposited in the cooling vessel.

The same procedures as those described in Example 55 were repeated several times by changing the temperature of the water in the cooling vessel from 20° to 90° C., while maintaining the pH of the water in the vessel at a level of 5.0. The relationship between the cooling temperature and the yield of malononitrile is indicated in FIG. 1. In the case where the temperature of the water in the vessel is 60° C. or more, a trap was arranged at the outlet of the cooling vessel and cooled with a dry ice-methanol coolant, so as to allow the vapor generated in the vessel to condense in the trap. The condensation was incorporated into the water in the vessel and a portion of the incorporated water was subjected to the gas chromatographic analysis.

Separately, the same procedures as those described in Example 55, were repeated several times by adjusting the pH of the water in the vessel to a value of from 1.0 to 10, while maintaining the temperature of the water at 30° C. The adjustment of the pH was carried out by using an aqueous sulfuric acid solution.

Figure 2:
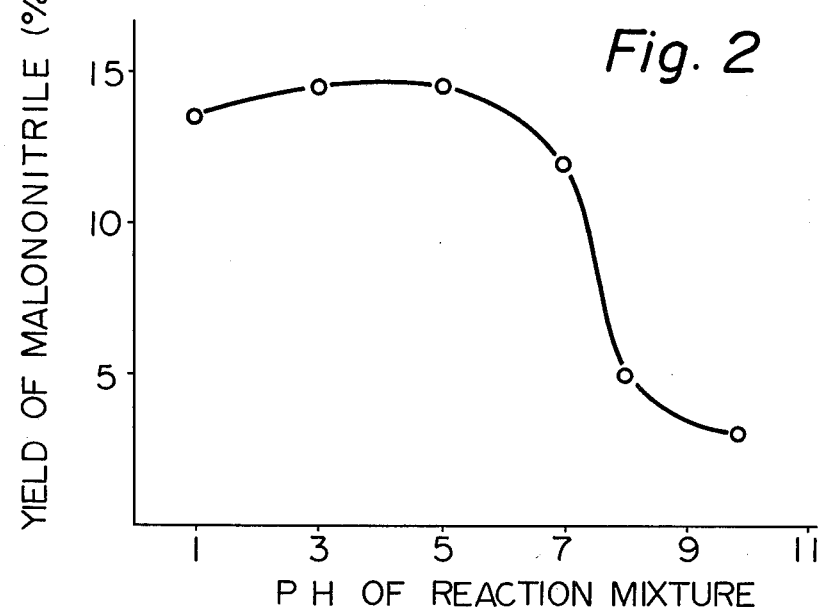
FIG. 2 is a graph showing a relationship between the pH of a reaction mixture and the yield of malononitrile.

The relationship between the pH of the water in the vessel and the yield of malononitrile is indicated in FIG. 2.

From FIGS. 1 and 2, it is clear that, in order to obtain malononitrile in a high yield, it is preferable that the reaction mixture be rapidly cooled to a temperature of 80° C. or less, more preferably, 60° C. or less, and that the pH of the malononitrile be maintained at a value of 0.7 or less, more preferably, 1.0 to 6.0.

COMPARATIVE EXAMPLE 2

The same procedures as those described in Example 55 were carried out, except that the feed gas contained β-aminopropionitrile, ammonia, molecular oxygen, nitrogen and steam in the molar ratio of 1:5:1.2:10:1.

The yield of malononitrile absorbed by the water in the cooling vessel was 5.4%. However, the yield of malononitrile, determined by using a portion of the resultant reaction mixture collected at the outlet of the reaction tube, was 9.8%, which is remarkably larger than the above-mentioned yield of 5.4%. From this phenomenon, it is clear that the ammonia contained in the feed gas causes the resultant malononitrile to be modified in the absorbing water.

We claim:

1. A method for catalytically producing malononitrile, comprising subjecting β-aminopropionitrile to an oxidative dehydrogenation in the absence of ammonia in a gaseous phase with molecular oxygen at a temperature of from 350° C. to 550° C. in the presence of a catalyst comprising at least one member selected from the group consisting of molybdenum oxide and oxide compositions of molybdenum and at least one member selected from the group consisting of titanium, vanadium, chromium, manganese, iron, cobalt, nickel, aluminum, tin, antimony, tellurium, bismuth, thallium, phosphorous, boron, alkali metals, alkaline earth metals, and rare earth metals.

2. A method as claimed in claim 1, wherein the molar ratio of β-aminopropionitrile to oxygen is in the range of from 1:0.5 to 1:10.

3. A method as claimed in claim 1, wherein the reaction mixture is rapidly cooled to a temperature of 80° C. or less to allow the resultant malononitrile to condense.

4. A method as claimed in claim 3, wherein the pH of the resultant condensate is adjusted to a value of 7.0 or less.

5. A method for catalytically producing malononitrile, comprising subjecting β-aminopropionitrile to an oxidative dehydrogenation in the absence of ammonia in the gaseous phase with molecular oxygen at a temperature of from 350° C. to 550° C. in the presence of a catalyst consisting essentially of an oxide composition of the empirical formula (I):

$$Mo_{12}Bi_{0.1-24}A_aB_bC_cD_dO_x \qquad (I)$$

wiherein A represents at least one member selected from the group consisting of iron and chromium; B represents at least one member selected from the group consisting of nickel, cobalt, magnanese and magnesium; C represents at least one member selected from the group consisting of alkali metals, alkaline earth metals, rare earth metals, tellurium, thallium, tungsten and lead; D represents at least one member selected from the group consisting of phosphorus, arsenic and boron; a represents the number 0.1 to 24; b represents the number 0 to 24; c represents the number 0 to 2; d represents the number 0 to 5; and, x represents the number of oxygen atoms which satisfies the valency of the catalytic elements in the oxide composition.

* * * * *